(12) United States Patent
Ezekiel (10) Patent No.: US 7,892,823 B2
(45) Date of Patent: Feb. 22, 2011

(54) METHODS AND SYSTEMS FOR HIGH HOMOLOGOUS RECOMBINATION ("HR") TARGETING EFFICIENCY

(75) Inventor: Uthayashanker Ezekiel, St. Louis, MO (US)

(73) Assignee: Geneprotech, Inc., St. Louis, MO (US)

( * ) Notice: Subject to any disclaimer, the term of this patent is extended or adjusted under 35 U.S.C. 154(b) by 853 days.

(21) Appl. No.: 11/702,865

(22) Filed: Feb. 6, 2007

(65) Prior Publication Data

US 2008/0187999 A1 Aug. 7, 2008

(51) Int. Cl.
*C12N 15/63* (2006.01)
*C12N 15/11* (2006.01)

(52) U.S. Cl. .................. 435/320.1; 536/23.1
(58) Field of Classification Search ........................ None
See application file for complete search history.

(56) References Cited

U.S. PATENT DOCUMENTS 6,045,997 A * 4/2000 Futreal et al. .................. 435/6
2005/0214944 A1* 9/2005 Zarling et al. ............... 435/455

OTHER PUBLICATIONS

Cao et al. Killing effect of coexpressing cytosine deaminase and thymidine kinase on rat vascular smooth muscle cells. Chin Med J (Engl). Oct. 2004; 117(10):1464-70.*
Galkin et al. BRCA2 BRC motifs bind RAD51-DNA filaments. Proc Natl Acad Sci U S A. Jun. 14, 2005;102(24):8537-42. Epub Jun. 3, 2005.*
Shivji et al. A region of human BRCA2 containing multiple BRC repeats promotes RAD51-mediated strand exchange. Nucleic Acids Res. 2006;34(14):4000-11. Epub Aug. 16, 2006.*

* cited by examiner

*Primary Examiner*—Michele K Joike
(74) *Attorney, Agent, or Firm*—Joseph E. Zahner

(57) ABSTRACT

Disclosed are vectors, kits and methods useful in the construction of recombinant cells and DNAs via enhanced efficiency homologous recombination. The vectors are targeting vectors that contain a gene-of-interest spliced between two ends that are homologous to a genome target site. The ends of the vector may be protected from exonuclease attack by deploying a cap, such as a hair pin structure. The vector is linked to a nuclear localization signal sequence, and preferably, a bait peptide that binds to RAD51, to facilitate homologous recombination. The vector may be deployed in myriad genetic transformation applications, such as site-directed mutagenesis, gene therapy, and the like.

9 Claims, 5 Drawing Sheets

SEQUENCE LISTING

<160> NUMBER OF SEQ ID NOS: 10

<210> SEQ ID NO 1
<211> LENGTH: 69
<212> TYPE: PRT
<213> ORGANISM: Murine

<400> SEQUENCE: 1

Glu Arg Asn Ile Lys Glu Phe Asn Ile Ser Phe Gln Thr Ala Ser Gly
1               5                   10                  15

Lys Asn Thr Arg Val Ser Lys Glu Ser Leu Asn Lys Ser Val Asn Ile
            20                  25                  30

Phe Asn Arg Glu Thr Asp Glu Leu Thr Val Ile Ser Asp Ser Leu Asn
        35                  40                  45

Ser Lys Ile Leu His Gly Ile Asn Lys Asp Lys Met His Thr Ser Ser
    50                  55                  60

His Lys Lys Ala Cys
65

<210> SEQ ID NO 2
<211> LENGTH: 66
<212> TYPE: PRT
<213> ORGANISM: Murine

<400> SEQUENCE: 2

Tyr Glu Ile Glu Ser Thr Lys Glu Pro Thr Leu Leu Ser Phe His Thr
1               5                   10                  15

Ala Ser Gly Lys Lys Val Lys Ile Met Gln Glu Ser Leu Asp Lys Val
            20                  25                  30

Lys Asn Leu Ser Gly Glu Thr Gln Tyr Val Arg Lys Thr Ala Ser Phe
        35                  40                  45

Ser Gln Gly Ser Lys Pro Leu Lys Asp Ser Lys Glu Leu Thr Leu
    50                  55                  60

Ala Cys
65

<210> SEQ ID NO 3
<211> LENGTH: 52
<212> TYPE: PRT
<213> ORGANISM: Murine

<400> SEQUENCE: 3

Val Ala Ala Lys His Ala Ala Val Leu Pro Ala Pro Lys His Ser
1               5                   10                  15

Thr Pro Val Thr Ala Ala Ser Glu Leu Leu Gln Glu Lys Val Val Phe
            20                  25                  30

Pro Asp Asn Leu Glu Glu Asn Leu Glu Met Trp Asp Leu Thr Pro Asp
        35                  40                  45

Leu Glu Asp Cys
    50

<210> SEQ ID NO 4
<211> LENGTH: 52
<212> TYPE: PRT
<213> ORGANISM: Murine

```
<400> SEQUENCE: 4

Ser Ser Tyr Pro Val Thr Glu Asp Ser Ala Leu Ala Tyr Tyr Thr Glu
1               5                   10                  15

Asp Ser Arg Lys Thr Cys Val Arg Glu Ser Ser Leu Ser Lys Gly Arg
            20                  25                  30

Lys Trp Leu Arg Glu Gln Gly Asp Lys Leu Gly Thr Arg Asn Thr Ile
        35                  40                  45

Lys Ile Glu Cys
    50

<210> SEQ ID NO 5
<211> LENGTH: 11
<212> TYPE: PRT
<213> ORGANISM: Artificial
<220> FEATURE:
<223> OTHER INFORMATION: synthetic

<400> SEQUENCE: 5

Pro Lys Lys Lys Arg Lys Val Glu Asp Pro Cys
1               5                   10

<210> SEQ ID NO 6
<211> LENGTH: 37
<212> TYPE: DNA
<213> ORGANISM: Artificial
<220> FEATURE:
<223> OTHER INFORMATION: synthetic

<400> SEQUENCE: 6
ggccgcgatg tgactcgctt tttgcgagtc acatcgc                             37

<210> SEQ ID NO 7
<211> LENGTH: 35
<212> TYPE: DNA
<213> ORGANISM: Artificial
<220> FEATURE:
<223> OTHER INFORMATION: synthetic

<400> SEQUENCE: 7
ccgatgtgac tcgtttttcg agtcacatcg gccgg                               35

<210> SEQ ID NO 8
<211> LENGTH: 79
<212> TYPE: PRT
<213> ORGANISM: Artificial
<220> FEATURE:
<223> OTHER INFORMATION: synthetic

<400> SEQUENCE: 8

Pro Lys Lys Lys Arg Lys Val Glu Asp Pro Gly Ser Gly Tyr Glu Ile
1               5                   10                  15

Glu Ser Thr Lys Glu Pro Thr Leu Leu Ser Phe His Thr Ala Ser Gly
            20                  25                  30

Lys Lys Val Lys Ile Met Gln Glu Ser Leu Asp Lys Val Lys Asn Leu
        35                  40                  45

Ser Gly Glu Thr Gln Tyr Val Arg Lys Thr Ala Ser Phe Ser Gln Gly
    50                  55                  60

Ser Lys Pro Leu Lys Asp Ser Lys Glu Leu Thr Leu Ala Cys
65                  70                  75
```

```
<210> SEQ ID NO 9
<211> LENGTH: 8
<212> TYPE: PRT
<213> ORGANISM: Homo sapiens

<400> SEQUENCE: 9

Gly Glu Phe Arg Thr Gly Lys Thr
1               5

<210> SEQ ID NO 10
<211> LENGTH: 5
<212> TYPE: PRT
<213> ORGANISM: Homo sapiens

<400> SEQUENCE: 10

Leu Leu Ile Val Asp
1               5
```

METHODS AND SYSTEMS FOR HIGH HOMOLOGOUS RECOMBINATION ("HR") TARGETING EFFICIENCY

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND

1. Field of the Invention

The invention is directed generally to genetic engineering methods and systems, and specifically to efficient methods and systems of gene targeting and integration of genes into a genome.

2. Description of the Related Art

Homologous recombination (HR) is at the heart of gene-targeting technologies. Technologies that increase the frequency of homologous recombination increase gene-targeting efficiency [1]. Applications of gene targeting technologies include gene knockouts and gene replacements in animals, cell model systems and gene therapies involving modification(s) of defective genes. Targeted homologous recombination (gene targeting) is widely used in murine embryonic stem (ES) cells as a method to ablate or introduce mutations into endogenous genes [2]. The subsequent transmission of the targeted alleles in ES cells into the mouse germ line provides a powerful method for studying gene function and has resulted in the creation of several critical mouse models for a variety of diseases [3, 4].

Development of efficient gene targeting methods for ES and somatic cells will greatly expand the use of gene replacement as a tool for researchers in their studies. Replacement of gene segment(s) known to cause disease in humans or gene ablation in human ES cells or adult somatic cells will pave the way to understanding biological processes and help in identifying causes and cures of diseases. Gene targeting in human ES and somatic cells has important applications in areas where rodent models do not adequately recapitulate human biology or disease progression. However, those applications require targeting frequencies much above the 0.1% levels achievable with today's technology. Currently, gene therapy mostly uses viral mediated approaches, which although successful, also can lead to serious complications [5]. While viral vectors provide efficient gene delivery, their main limitations are in areas of safety, in part because random integration of the vector may cause inactivation or activation of endogenous genes leading to potentially serious side effects [5, 6]. For example, in a retroviral mediated gene therapy clinical trial of ten children with X-linked SCID (IL-2 receptor γ chain defect), three of the children developed acute lymphoblastic leukemia due to insertion of the vector close to the LMO2 proto-oncogene [7, 8]. Therefore, the best biological approach for gene therapy is HR.

When DNA is introduced into mammalian cells by transfection, the cell machinery integrates transfected DNA into the genome by one of two routes: (1) a HR pathway in which the introduced DNA replaces the endogenous genomic sequences; and (2) a non-homologous pathway leading to random integration. The RAD51 gene of eukaryotes is a homologue of the E. coli recA gene and plays a crucial role in HR [12, 13]. The HR pathway entails pairing of homologous DNAs, strand exchange between them, and resolution of one or more Holliday junctions. A network of interacting proteins catalyzes each step [14]. RAD51 provides the enzymatic functions for recognition of homology and DNA strand exchange in HR. RAD51 binds and polymerizes onto the introduced DNA in a step called presynapsis. In the next step, the RAD51 nucleoprotein filament searches for homologous regions in chromosomal DNA, catalyzes pairing between introduced and endogenous DNA, and promotes strand exchange [13, 15].

Figure 1:
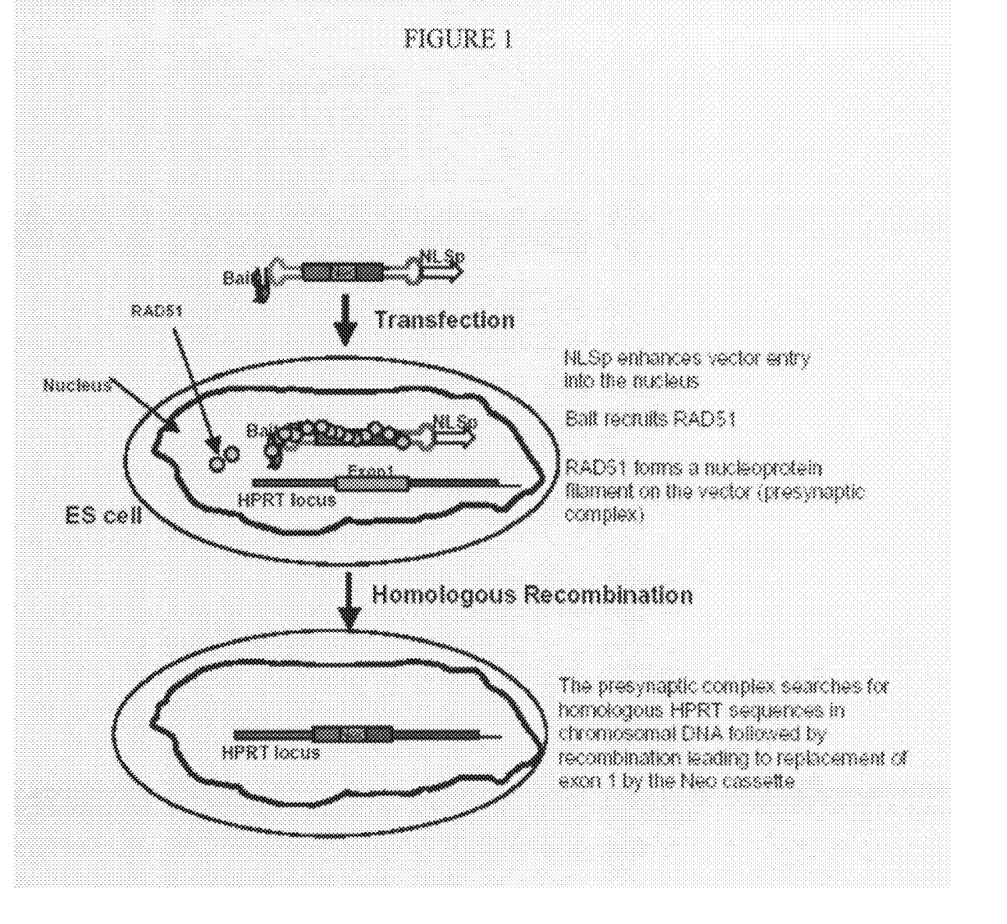
FIG. 1. Diagram for the enhancement of homologous recombination at the HPRT locus in ES cells by attachment of a bait peptide to the targeting vector. The bait peptide binds RAD51 thereby enhancing nucleation and polymerization of RAD51 onto the targeting DNA. A peptide containing a nuclear localization signal (NLSp) enhances trafficking of the vector into the nucleus. The homologous recombinant is resistant to cell death by 6-thioguanine because it lacks HPRT enzymatic activity and is resistant to G418 because of the chromosomal integration of neomycin resistant gene (Neo) carried in the targeting vector.

The amino acids at the N-terminal region of RAD51 are highly conserved among species and form a domain involved in the oligomerization of RAD51 for nucleoprotein filament formation [16]. Besides RAD51, RAD52 and Replication Protein A (RPA), together known as "the catalytic triad" of proteins, are also involved in filament formation [17]. HR is mediated by double strand breaks in the recombining DNAs and RPA binds and protects the single strand ends until they are coated with RAD51. RAD51 then forms a helical nucleoprotein filament on the single strand DNA—a process facilitated by RAD52 displacement of RPA. Genetic and biochemical studies indicate that RAD51 interacts with both RAD52 and RPA [14, 18]. Another protein involved in RAD51 function is BRCA2. The conserved BRC domains within BRCA2 bind RAD51 and it is thought that this interaction recruits RAD51 to sites of DNA damage, thereby promoting repair and/or recombination [19]. Cells transiently over-expressing either recA or RAD51 (2-fold over-expression) show some 20-fold elevation in the frequencies of HR, suggesting that efficient nucleoprotein filament formation is a rate limiting step in HR [1, 20]. The novel approach taken in this proposal to increase the frequency of HR involves covalently attaching a RAD51 binding peptide to the targeting vector so as to promote nucleation and polymerization of RAD51 onto the transfected DNA. By analogy to the function of BRCA2, the recruitment of RAD51 to the targeting DNA is expected to increase nucleoprotein filament formation and thereby HR (FIG. 1).

Three proteins, RAD52, RPA and BRCA2 have been shown to interact physically with RAD51 [19, 21, 22]. Most of the studies regarding RAD52 function come from studies done in yeast, where both genetic and molecular studies clearly demonstrate its binding to the N-terminal region of RAD51 and its role in HR and repair of double strand DNA breaks [23]. Interaction between the human RAD52 and RAD51 proteins has been demonstrated in the yeast two hybrid system, by their co-immunoprecipitation when expressed in either HeLa or insect cells, and by affinity column chromatography [21, 24, 25]. By deletion analysis, the domain within RAD52 that binds RAD51 has been mapped to amino acid residues 291-330 of the human RAD52 [21].

RPA is a heterotrimer consisting of 70, 32 and 14 kDa subunits and it is the 70 kDa subunit which binds to RAD51 [17, 22]. At sites of DNA damage, RPA binds to single strand DNA and protects the exposed DNA ends until they can be coated by RAD51. RPA also removes secondary structures that prevent extension of nucleoprotein filament formation by RAD51. NMR chemical shift mapping indicates that residues 1-93 at the N terminus of RAD51 interact with the DNA binding region of the 70 kDa subunit of RPA in a domain defined by residues 181-326 [26].

Human BRCA2 is a very large protein (3418 amino acids) but its RAD51 binding domains appear to reside within a set of eight conserved repeats (termed BRC1-8) each about 70 amino acids in length [27, 28]. Mutations within this eight-repeat region are associated with a predisposition to cancer and reduced DNA repair [29, 30]. Recent reports indicate that although the repeats are homologous, they appear to bind RAD51 at different regions of the protein. BRC3 (residues 1415-1483) binds to the N-terminal region of RAD51, whereas BRC4 (residues 1511-1579) binds to the nucleotide binding core of RAD51 located in the middle of that protein (residue 127-135:GEFRTGKT [SEQ ID NO:9] and 228-232: LLIVD [SEQ ID NO:10]) [27, 28]. That finding is important for this proposal because it suggests that a targeting vector containing both the BRC3 and BRC4 domains may recruit RAD51 in vivo much more efficiently due to cooperative binding. Furthermore, BRC5 (residues 1618-1670) does not appear to interact with RAD51, despite its homology to the other BRC repeats. The interaction of BRC repeats with RAD51 was shown using peptides (~69 amino acids in length) corresponding in sequence to a given BRC repeat. These studies also demonstrated that shorter peptides (~30 amino acids in length) corresponding to the central conserved motif of the BRC repeats were not effective for RAD51 binding [27]. This observation forms the rationale for coupling the full-length RAD51 binding domain to the targeting DNA as "bait" for the recruitment of RAD51.

Blocking DNA ends so as to prevent exonucleolytic degradation has been shown to reduce unwanted random integration, and in Dictyostelium discoideum, to increase site-specific targeting events [31]. According to the present invention, the ends of the targeting DNA are blocked by ligation of a hairpin oligonucleotide so as to eliminate free 3' or 5' ends. Another avenue for increased gene targeting is based on more effective gene delivery to the nucleus where HR takes place. Several attempts to improve the entry of plasmid DNA into the nucleus have been reported including "piggyback" techniques like electrostatic binding of DNA to cationic proteins containing a nuclear localization signal (NLS) [32, 33], NLS-containing peptides [34], lipids [35] and karyophilic proteins [36, 37]. A major drawback of this "piggyback" nuclear transport is that it relies upon the unpredictable stability of the complex in the cytoplasm [35]. In our case, we will covalently couple an NLS-containing peptide to one end of the targeting DNA.

Interestingly, DNAs tagged with a single NLS-peptide show enhanced delivery to the nucleus, but the presence of more than one NLS-peptide tag on a DNA molecule prevents gene delivery. This observation suggests that a DNA molecule with two NLS tags threads through two adjacent nuclear pores in a manner that leads to entrapment of the DNA at the nuclear membrane and consequent decreased gene delivery into the nucleus [35].

Targeting of a gene to the HPRT locus is desirable for gene therapy not only because it avoids the random insertional mutagenesis associated with viral mediated gene delivery, but also because extensive experience exists relevant to targeting genes to that locus. The HPRT gene is expressed in all cells and during all stages of development and is a locus that constitutively remains in an open chromatin configuration. Transgenic mice expressing human angiotensinogen from a gene targeted to the HPRT locus showed normal tissue expression and functionality at physiological levels [38].

The protein encoded by the HPRT gene (nine exons spread over a 33 Kb region of the X chromosome) is involved in the salvage pathway of nucleotide metabolism [9]. Cells with functional HPRT incorporate the nucleotide analogue 6-thioguanine (6-TG) into DNA, which leads to cell death. In the absence of HPRT, there is no incorporation of 6-TG into the nucleotide pool, thus, HPRT disrupted cells survive in the presence of 6-TG [9]. The HPRT locus has been used as a target for the study of various aspects of HR. In one study, the influence of homology length in the targeting vector and its targeting efficiency was compared using the HPRT locus. Deng and Capecchi [39] demonstrated similar targeting frequencies in vectors of different homology lengths. Zhang et al [40] evaluated HR frequencies as a function of the endogenous size of the deletion region that occurs upon insertion of targeting vectors. Hatada et al used targeting to the HPRT locus to show that HR frequencies are similar in ES cells versus hematopoietic progenitor cells [11].

Since the HPRT targeting vector contains a neomycin resistance marker, both random and targeted integration events will confer resistance to the antibiotic G418. However, when cells are grown in the presence of G418 plus 6-TG, only cells with a targeted disruption of the HPRT locus will survive. Therefore, there are two ways recombination frequencies can be expressed: (1) targeted cells (those that are G418 and 6-TG resistant) divided by the total number of cells subjected to selection provides the overall recombination frequency; and (2) targeted cells (those that are G418 and 6-TG resistant) divided by the number of G418 resistant cells (i.e., both random and targeted recombination events) provides the targeted recombination frequency. Both methods of expression of recombination frequency appear in the literature. For example, a study using murine ES-D3 cells for HPRT gene targeting had overall recombination frequencies of $0.4 \times 10^{-6}$ and $1.6 \times 10^{-6}$ in two different experiments with targeted recombination frequencies of $1.3 \times 10^{-5}$ and $5.3 \times 10^{-5}$ respectively [41]. Whereas the targeted recombination frequency reports on the ratio of site-specific to random integration events, the overall recombination frequency reports on the total number of targeted integration events in the cell population. The invention uses both measures to evaluate the effects of the proposed modification to the targeting vector on HR. So, for example, we expect that attaching an NLS-signal peptide to the targeting vector will increase the overall recombination frequency but not necessarily site-specific targeting. On the other hand, vectors with an attached peptide bait that binds RAD51 should increase both site-specific targeting—i.e., increase the targeted recombination frequency—as well as the overall recombination frequency.

Current gene therapy using viruses has advantages, such as efficient gene delivery, but their main limitations are in the areas of safety and random integration events causing inactivation or activation of endogenous genes [6, 8, 42, 43]. The best biological approach for gene therapy therefore is HR where one either replaces the defective region of a gene with its normal counterpart or expresses a normal gene at a known locus thereby avoiding random insertional mutagenesis. Development of a method for efficient gene targeting will allow for rapid advancements in the creation of cells or cell lines containing modified genes for the purpose of studying the biological function of specific genes. Drawbacks to the use of HR in mammalian cells for gene targeting purposes are its inherent inefficiency and relatively low frequency of targeted integration.

CITED REFERENCES

The follow references are cited throughout this disclosure. They are incorporated herein in their entirety by reference. They are used for illustration purposes. Applicant reserves the right to challenge the veracity of any statement made therein.

[1] S. Vispe, C. Cazaux, C. Lesca and M. Defais, Overexpression of Rad51 protein stimulates homologous recombination and increases resistance of mammalian cells to ionizing radiation. Nucleic Acids Res 26, 2859-2864 (1998).

[2] M. R. Capecchi, Altering the genome by homologous recombination. Science 244, 1288-1292 (1989).

[3] T. E. Willnow and J. Herz, Homologous recombination for gene replacement in mouse cell lines. Methods Cell Biol 43 Pt A, 305-334 (1994).

[4] S. Thompson, A. R. Clarke, A. M. Pow, M. L. Hooper and D. W. Melton, Germ line transmission and expression of a corrected HPRT gene produced by gene targeting in embryonic stem cells. Cell 56, 313321 (1989).

[5] Y. Yi, S. H. Hahm and K. H. Lee, Retroviral gene therapy: safety issues and possible solutions. Curr Gene Ther 5, 25-35 (2005).

[6] S. Laufs, B. Gentner, K. Z. Nagy, A. Jauch, A. Benner, S. Naundorf, K. Kuehlcke, B. Schiedlmeier, A. D. Ho, W. J. Zeller and S. Fruehauf, Retroviral vector integration occurs in preferred genomic targets of human bone marrow-repopulating cells. Blood 101, 2191-2198 (2003).

[7] D. B. Kohn, M. Sadelain and J. C. Glorioso, Occurrence of leukaemia following gene therapy of X-linked SCID. Nat Rev Cancer 3, 477-488 (2003).

[8] H. B. Gaspar and A. J. Thrasher, Gene therapy for severe combined immunodeficiencies. Expert Opin Biol Ther 5, 1175-1182 (2005).

[9] D. W. Melton, D. S. Konecki, J. Brennand and C. T. Caskey, Structure, expression, and mutation of the hypoxanthine phosphoribosyltransferase gene. Proc Natl Acad Sci U S A 81, 2147-2151 (1984).

[10] S. K. Bronson, E. G. Plaehn, K. D. Kluckman, J. R. Hagaman, N. Maeda and O. Smithies, Single-copy transgenic mice with chosen-site integration. Proc Natl Acad Sci U S A 93, 9067-9072 (1996).

[11] S. Hatada, K. Nikkuni, S. A. Bentley, S. Kirby and O. Smithies, Gene correction in hematopoietic progenitor cells by homologous recombination. Proc Natl Acad Sci U S A 97, 13807-13811 (2000).

[12] T. Ogawa, A. Shinohara, A. Nabetani, T. Ikeya, X. Yu, E. H. Egelman and H. Ogawa, RecA-like recombination proteins in eukaryotes: functions and structures of RAD51 genes. Cold Spring Harb Symp Quant Biol 58, 567-576 (1993).

[13] P. Baumann and S. C. West, Role of the human RAD51 protein in homologous recombination and double-stranded-break repair. Trends Biochem Sci 23, 247-251 (1998).

[14] D. Jackson, K. Dhar, J. K. Wahl, M. S. Wold and G. E. Borgstahl, Analysis of the human replication protein A:Rad52 complex: evidence for crosstalk between RPA32, RPA70, Rad52 and DNA. J Mol Biol 321, 133-148 (2002).

[15] J. M. Stark, P. Hu, A. J. Pierce, M. E. Moynahan, N. Ellis and M. Jasin, ATP hydrolysis by mammalian RAD51 has a key role during homology-directed DNA repair. J Biol Chem 277, 20185-20194 (2002).

[16] K. A. Miller, D. Sawicka, D. Barsky and J. S. Albala, Domain mapping of the Rad51 paralog protein complexes. Nucleic Acids Res 32, 169-178 (2004).

[17] M. S. Park, D. L. Ludwig, E. Stigger and S. H. Lee, Physical interaction between human RAD52 and RPA is required for homologous recombination in mammalian cells. J Biol Chem 271, 18996-19000 (1996).

[18] T. Sugiyama and S. C. Kowalczykowski, Rad52 protein associates with replication protein A (RPA) single-stranded DNA to accelerate Rad51-mediated displacement of RPA and presynaptic complex formation. J Biol Chem 277, 31663-31672 (2002).

[19] B. J. Orelli and D. K. Bishop, BRCA2 and homologous recombination. Breast Cancer Res 3, 294-298 (2001).

[20] O. G. Shcherbakova, V. A. Lanzov, H. Ogawa and M. V. Filatov, Overexpression of bacterial RecA protein stimulates homologous recombination in somatic mammalian cells. Mutat Res 459, 65-71 (2000).

[21] Z. Shen, K. G. Cloud, D. J. Chen and M. S. Park, Specific interactions between the human RAD51 and RAD52 proteins. J Biol Chem 271, 148-152 (1996).

[22] E. I. Golub, R. C. Gupta, T. Haaf, M. S. Wold and C. M. Radding, Interaction of human rad51 recombination protein with single-stranded DNA binding protein, RPA. Nucleic Acids Res 26, 5388-5393 (1998).

[23] Y. Aylon and M. Kupiec, New insights into the mechanism of homologous recombination in yeast. Mutat Res 566, 231-248 (2004).

[24] J. H. New, T. Sugiyama, E. Zaitseva and S. C. Kowalczykowski, Rad52 protein stimulates DNA strand exchange by Rad51 and replication protein A. Nature 391, 407-410 (1998).

[25] T. Ogawa, A. Shinohara and T. Ikeya, A species-specific interaction of rad51 and rad52 proteins in eukaryotes. Adv Biophys 31, 93-100 (1995).

[26] M. E. Stauffer and W. J. Chazin, Physical interaction between replication protein A and RadS1 promotes exchange on single-stranded DNA. J Biol Chem 279, 25638-25645 (2004).

[27] V. E. Galkin, F. Esashi, X. Yu, S. Yang, S. C. West and E. H. Egelman, BRCA2 BRC motifs bind RADS1 DNA filaments. Proc Natl Acad Sci U S A 102, 8537-8542 (2005).

[28] M. K. Shivji, O. R. Davies, J. M. Savill, D. L. Bates, L. Pellegrini and A. R. Venkitaraman, A region of human BRCA2 containing multiple BRC repeats promotes RAD51-mediated strand exchange. Nucleic Acids Res 34, 4000-4011 (2006).

[29] A. Tutt and A. Ashworth, The relationship between the roles of BRCA genes in DNA repair and cancer predisposition. Trends Mol Med 8, 571-576 (2002).

[30] C. F. Chen, P. L. Chen, Q. Zhong, Z. D. Sharp and W. H. Lee, Expression of BRC repeats in breast cancer cells disrupts the BRCA2-Rad51 complex and leads to radiation hypersensitivity and loss of G(2)/M checkpoint control. J Biol Chem 274, 32931-32935 (1999).

[31] N. Shah-Mahoney, T. Hampton, R. Vidaver and D. Ratner, Blocking the ends of transforming DNA enhances gene targeting in Dictyostelium. Gene 203, 33-41 (1997).

[32] Y. Kaneda, K. Iwai and T. Uchida, Increased expression of DNA cointroduced with nuclear protein in adult rat liver. Science 243, 375-378 (1989).

[33] J. D. Fritz, H. Herweijer, G. Zhang and J. A. Wolff, Gene transfer into mammalian cells using histone condensed plasmid DNA. Hum Gene Ther 7, 1395-1404 (1996).

[34] P. Collas, H. Husebye and P. Alestrom, The nuclear localization sequence of the SV40 T antigen promotes transgene uptake and expression in zebrafish embryo nuclei. Transgenic Res 5, 451-458 (1996).

[35] M. A. Zanta, P. Belguise-Valladier and J. P. Behr, Gene delivery: a single nuclear localization signal peptide is sufficient to carry DNA to the cell nucleus. Proc Natl Acad Sci U S A 96, 91-96 (1999).

[36] J. Fominaya and W. Wels, Target cell-specific DNA transfer mediated by a chimeric multidomain protein. Novel non-viral gene delivery system. J Biol Chem 271, 10560-10568 (1996).

[37] D. A. Dean, Peptide nucleic acids: versatile tools for gene therapy strategies. Adv Drug Deliv Rev 44, 81 95 (2000).

[38] B. Cvetkovic, B. Yang, R. A. Williamson and C. D. Sigmund, Appropriate tissue- and cell-specific expression of a single copy human angiotensinogen transgene specifically targeted upstream of the HPRT locus by homologous recombination. J Biol Chem 275, 1073-1078 (2000).

[39] C. Deng and M. R. Capecchi, Reexamination of gene targeting frequency as a fuinction of the extent of homology between the targeting vector and the target locus. Mol Cell Biol 12, 3365-3371 (1992).

[40] H. Zhang, P. Hasty and A. Bradley, Targeting frequency for deletion vectors in embryonic stem cells. Mol Cell Biol 14, 2404-2410 (1994).

[41] T. Doetschman, N. Maeda and O. Smithies, Targeted mutation of the Hprt gene in mouse embryonic stem cells. Proc Natl Acad Sci U S A 85, 8583-8587 (1988).

[42] E. Check, Cancer fears cast doubts on future of gene therapy. Nature 421, 678 (2003).

[43] C. Baum, J. Dullmann, Z. Li, B. Fehse, J. Meyer, D. A. Williams and K. C. von, Side effects of retroviral gene transfer into hematopoietic stem cells. Blood 101, 2099-2114 (2003).

[44] D. R. Greaves, P. Fraser, M. A. Vidal, M. J. Hedges, D. Ropers, L. Luzzatto and F. Grosveld, A transgenic mouse model of sickle cell disorder. Nature 343, 183-185 (1990).

[45] A. Mortellaro, R. J. Hernandez, M. M. Guerrini, F. Carlucci, A. Tabucchi, M. Ponzoni, F. Sanvito, C. Doglioni, S. C. Di, L. Biasco, A. Follenzi, L. Naldini, C. Bordignon, M. G. Roncarolo and A. Aiuti, Ex vivo gene therapy with lentiviral vectors rescues adenosine deaminase (ADA)-deficient mice and corrects their immune and metabolic defects. Blood 108, 2979-2988 (2006).

[46] S. Sekhsaria, J. I. Gallin, G. F. Linton, R. M. Mallory, R. C. Mulligan and H. L. Malech, Peripheral blood progenitors as a target for genetic correction of p47phox-deficient chronic granulomatous disease. Proc Natl Acad Sci U S A 90, 7446-7450 (1993).

[47] S. I. Grewal and A. J. Klar, A recombinationally repressed region between mat2 and mat3 loci shares homology to centromeric repeats and regulates directionality of mating-type switching in fission yeast. Genetics 146, 1221-1238 (1997).

[48] X. Liu and D. F. Barker, Evidence for effective suppression of recombination in the chromosome 17q21 segment spanning RNU2-BRCA1. Am J Hum Genet 64, 1427-1439 (1999).

[49] A. K. Wong, R. Pero, P. A. Ormonde, S. V. Tavtigian and P. L. Bartel, RAD51 interacts with the evolutionarily conserved BRC motifs in the human breast cancer susceptibility gene brca2. J Biol Chem 272, 31941-31944 (1997).

[50] T. A. Tatusova and T. L. Madden, BLAST 2 Sequences, a new tool for comparing protein and nucleotide sequences. FEMS Microbiol Lett 174, 247-250 (1999).

[51] C. Gauthier-Rouviere, M. Vandromme, N. Lautredou, Q. Q. Cai, F. Girard, A. Fernandez and N. Lamb, The serum response factor nuclear localization signal: general implications for cyclic AMP-dependent protein kinase activity in control of nuclear translocation. Mol Cell Biol 15, 433-444 (1995).

SUMMARY OF THE INVENTION

The inventor has succeeded in developing methods and systems for high homologous recombination ("HR") targeting efficiency with relative technical ease of use. The methods and systems comprise the use of and inclusion of (respectively) targeting vectors that comprises (a) an insertion polynucleotide sequence encoding a gene-product-of-interest (e.g., an enzyme for gene therapy; a selectable marker such as neomycin resistance [neo$^r$]; gene-product-of-interest is not limiting in its scope beyond genes, thus it can be any polynucleotide, polypeptide, regulatory sequence, intron, exon, RNAi locus, et cetera), (b) a proximal target polynuceotide, which has homology to a proximal portion of a target polynucleotide sequence, (c) and a distal target polynucleotide, which has homology to the distal portion of the target polynucleotide sequence, (d) a nuclear localization signal ("NLS") sequence, which allows the entire targeting vector to enter the nucleus of a transfected cell. In a preferred embodiment, the ends of the targeting vector are blocked to prevent exonucleolysis. Preferred blocking groups are hair pin loops of nucleic acid, but other means may be used in the practice of the invention. In a more preferred embodiment, the targeting vector comprises a bait peptide attached to the end of the targeting vector that is distal to the end to which the NLS is attached. The bait peptide is an amino acid sequence that enables the targeting vector to bind to the homology recognition machinery (which includes the catalytic triad [supra]) of the cell. Preferred bait peptides recognize RAD51 (recA). More preferred bait peptides comprise or consist of, or consist essentially of peptides having a sequence that is at least 70% identical to SEQ ID NOs. 1-3. In yet another aspect, the targeting vector may comprise additional bait polypeptides, to enhance cooperativity and even greater efficiency of homologous recombination. Bait peptides can be a "universal" bait that works in a variety of systems, or species-specific bait polypeptides.

Thus the invention is directed to a targeting vector for efficient homologous recombination ("HR"). In another embodiment, the invention is directed to a kit, which comprises an hp-peptide ready for ligation to targeting vectors for the purpose of efficient targeting. The kit further comprises instructions, buffers and enzymes required for the construction of a custom end-user targeting vector. In yet another embodiment, the invention is directed to an efficient non-viral targeting method to create vectors and cells for gene therapy. The method is also applicable to engineer "humanized" mice, that is, mice in which a human gene has been "knocked in" to replace the corresponding mouse gene; to target the animal genome with known modifications is of interest to individuals in the cattle and dairy as well as other animal-related industries; and other applications for directed gene insertion.

The invention herein discloses improved HR by increasing HR frequency at the HPRT locus so that the HPRT locus may be used as a universal docking site for gene therapy. However, the invention shall not be limited to dropping in genes at the HPRT site. The HPRT site is useful as an example and as a handy "universal" target site. For example, in hematopoietic monogenic diseases such as sickle cell anemia [44], SCID (due to deaminase deficiency) [45] and chronic granulomatous disease (due to defective NADP oxidase) [46], according to this invention, expression of the respective normal gene at the HPRT locus is reasonably expected to significantly improve disease symptoms. Bone marrow or hematopoietic cells are isolated from a patient and used in vitro for targeting of the normal functioning gene to the HPRT docking site. Targeted cells are then selected by growth in 6-TG, and after expansion, transferred back into the patient. Mouse models for single gene diseases (such as SCID and NADP oxidase deficiency) can be used to test the feasibility of autologous gene targeting at the HPRT locus.

Another non-limiting application for the present invention is in targeting genes to genetic loci that are refractory to HR. If the bait present on the targeting vector shows an increase in HR frequency at the HPRT locus, then that bait may also be useful in gene targeting to loci that are usually refractory for HR. For example, genes located in repeat scattered regions or close to centromeric regions do not respond well to gene targeting strategies since HR in repeat regions is suppressed [47, 48]. This HR suppression may be the reason that certain mouse models are difficult to make by currently available gene targeting methodologies. An embodiment of the instant invention is a commercial targeting kit that contains two hairpin oligonucleotides, one with the NLS-peptide and the other with the bait peptide. All that will remain for the consumer in the practice of the invention is the ligation of those peptide-containing oligonucleotides to a linear targeting vector followed by transfection.

BRIEF DESCRIPTION OF THE DRAWINGS

FIG. 2. Structure of the HPRT targeting vector. The 5' and 3' genomic regions that flank the HPRT promoter-exon 1 region are represented in the vector. The neomycin resistance gene (NEO) contained within the targeting vector is driven by the PGK1 promoter. To the ends of the targeting vector are ligated hairpin oligonucleotides via sticky ends created by FseI (left) and NotI (right) digestion of the targeting DNA. Hairpin oligonucleotides contain an alkylamino modified T residue for coupling to the various peptides discussed in the text. Peptides are ligated to hairpin oligonucleotides before their ligation to the targeting vector.

FIG. 3. Gene Targeting at the HPRT locus. Homologous recombination mediated at the HPRT genomic locus results in the deletion of the 4 kbp-promoter exon 1 region (green box) with concomitant replacement by the 2 kbp neomycin cassette (NEO). The crosses (x) between the targeting vector and the genomic locus depict homologous recombination. The expected DNA fragment sizes after HindIII (H) digestion of wild type versus recombinant DNA are shown (10.2 kbp and 8.2 kbp, respectively). The position of a 5' probe to detect wild-type versus recombinant HindIII digestion products by Southern analysis is depicted by short box in bold.

FIG. 4. Screening strategy for homologous recombination at the HPRT locus. HindIII digestion of wild-type (wt) genomic DNA produces a 10.2 kbp DNA fragment (lane 1), whereas HindIII digestion of recombinant 10.2 Kbp(Rec) DNA resulting from gene targeting at the HPRT locus produces an 8.2 Kbp 8.2 kb DNA fragment (lane 2). Arrows point to bands of 10.2 kbp and 8.2 kbp sizes. F9 embryonic carcinoma cells used in this experiment were of normal karyotype with respect to XY chromosomes. Since the HPRT gene is located in the X chromosome, only an 8.2 kbp band is seen in the Southern blot.

FIG. 5. Structure of control and bait vectors. The hairpin oligonucleotide in red is ligated to the NotI end of the vectors, and the hairpin oligonucleotide in green is ligated to the FseI end of the vectors. All vectors have a nuclear localization signal peptide (NLSp—11 amino acids in length) ligated to the NotI end. All bait vectors have bait peptides ligated to the FseI end. BRC3, BRC4, and RAD52 indicate peptides derived from BRCA2 and RAD52 that bind RAD51. BRC5 indicates a peptide derived from BRCA2 which does not bind RAD51. All bait peptides are between 52-69 amino acids in length.

DESCRIPTION OF A PREFERRED EMBODIMENT OF THE INVENTION

The invention is directed to kits, vectors and methods for high HR targeting efficiency with technical ease of performance. Since several studies have reported successful targeting in mouse ES cells, those cell types are used to exemplify in a non-limiting way, the practice of this invention. HR frequency is generally assessed by targeting to the hypoxanthine phosphoribosyl transferase (HPRT) locus [9]. The HPRT locus offers several advantages as a target docking site for gene therapy applications [10, 11]: (1) Its open chromatin configuration ensures expression of genes integrated there; (2) Since HPRT enzymatic activity is dispensable (HPRT knockout mice display normal phenotypes), integration of a targeted gene into that locus is not in and of itself deleterious; and (3) Powerful selection methods are available to select for and isolate cells having the targeted gene integrated at the HPRT locus—and likewise to select against integration events outside of that locus. HPRT functions in the salvage nucleotide pathway. Cells with a mutated HPRT gene survive when grown in the presence of the nucleotide analogue, 6-thioguanine (6-TG), but cells with a wild-type HPRT do not. Thus, growth in 6-TG selects for cells with HPRT-specific gene integration and against cells with gene integration elsewhere. If the targeted gene cassette also includes the neomycin resistance gene, then growth in G418 (a neomycin analogue) may also be utilized to first select for cells with an integrated target gene before negative selection using 6-TG. Therefore increasing HR frequencies at the HPRT locus can make this locus a universal docking site for chromosomal integration of a gene of interest.

While not wishing to be limited by theory, the invention is based upon the concept that HR frequencies can be greatly increased by using targeting vectors that are modified so as to contain two different peptides that in concert function to promote HR. The first peptide consists of a nuclear localization signal which increases the amount of transfected DNA trafficked into the nucleus. The second peptide acts to bind and recruit onto the targeting DNA RAD51 (the mammalian analogue of the bacterial recA protein), thereby promoting sequence-specific synapsis between the targeting DNA and homologous chromosomal sequences, and in turn HR.

The inventor has established an experimental system to assess frequency of recombination in a linear targeting vector with modified ends, which clearly demonstrated that a targeting vector with one end covalently attached to a nuclear localization peptide (NLSp) has an increased frequency of HR. A reasonable explanation for the increased HR frequency is that the targeting vector with NLSp enters the nucleus more frequently than does the control thereby making more substrate available in the nucleus for use by the HR machinery.

The following examples provided the current best mode and preferred embodiment of the instant invention. They are meant to illustrate the invention and not meant to limit the scope of the invention. The skilled artisan in the practice of this invention will readily recognize that other vectors, constructs, cell lines, and HR sites can be used while remaining within the spirit and scope of the invention, which is set forth in the claims which follow.

EXAMPLE 1

Targeting Vectors

Figure 2:
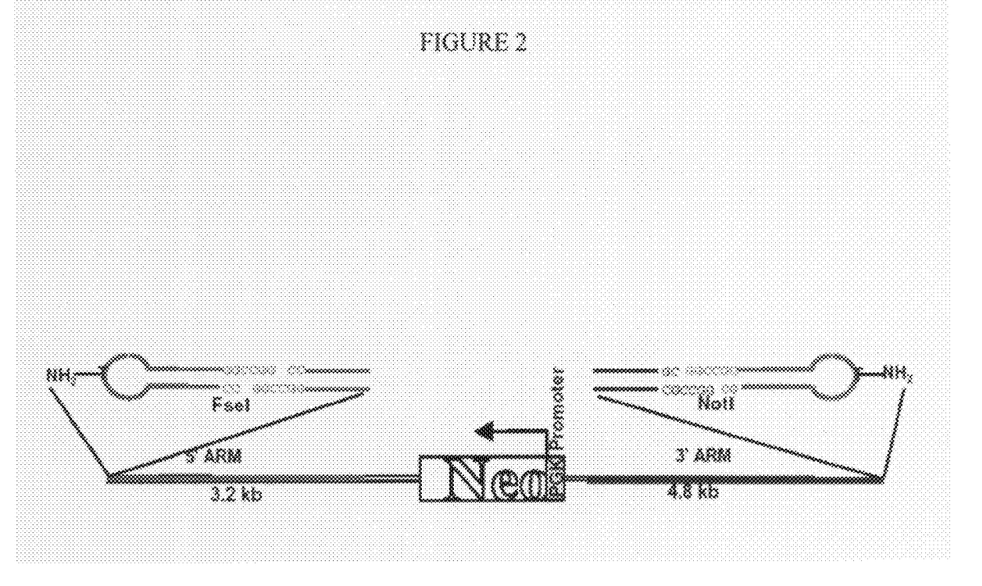

Modified targeting vectors contain hairpin oligonucleotides on each end with or without attached peptides. Briefly, hairpin oligonucleotides are made with a central T nucleotide containing an alkyamino group to which peptides are attached by a chemical method. The peptide NLSp was made with a C terminal cysteine. The amino group in the hairpin region is linked to the peptide containing a C terminal cysteine by a heterobifunctional cross linker. Before ligation, the hairpin structure of the oligonucleotide presenting a 5' sticky end was obtained by boiling and cooling on ice. The hairpin was ligated to the ends of the vector containing the corresponding sticky ends of the restriction site (FIG. 2). The reason for blocking the linear ends of the vector with hairpin oligonucleotides is to prevent the linear plasmid from forming concatemeric structures which will lead to spurious modification at the targeting locus. Additionally, blocking ends of a targeting vector has been suggested to help in preventing the targeting vector from entering into the nonhomologous recombination pathway [31]

HPRT Targeting Vector Construction

Modified pUC 19 plasmids have been made and used as the backbone for target vector construction. Plasmid pUC19 was digested by AatII and AflIII restriction enzymes. This digestion produced two DNA fragments: 1) a 0.875 Kb fragment that contains the polylinker cloning site and lacZ gene of pUC19; and 2) a 1.81 Kb fragment which contains the β-lactamase gene and the origin of replication. To the 1.81 Kb DNA fragment, several restriction sites were added by sequential ligation of oligolinkers thereby creating plasmid pUT1. FIG. 2 shows the HPRT targeting vector. The pUT1 backbone was used to construct the targeting vector. To make the targeting vector, the 5' and 3' homologous regions flanking the 5' region of the promoter (3.5 Kb, red line) and the 3' region of exon 1 (4.8 Kb, blue line) were used as a homologous arm in the targeting vector (FIG. 2). Since transcription of the HPRT gene requires the promoter region, the targeting vector was designed such that HR of this vector at the HPRT locus eliminates the promoter-exon 1 region thereby completely eliminating HPRT gene expression. The 5' XbaI fragment (3.5 Kbp) was cloned into a pUT1 plasmid at the XbaI site and 3' DNA fragment EcoRV-EcoRI (4.8 Kbp) subjected to a fill-in reaction and cloned at the Ecl136II site. At the EcoRV site of pUT1 containing 5' and 3' arms, a Neor selection gene was cloned. The presence of the phosphoglycerate kinase 1 (PGK1) promoter allows for constitutive expression of the Neo$_r$ gene.

HPRT Targeting Vector Modification

Figure 3:
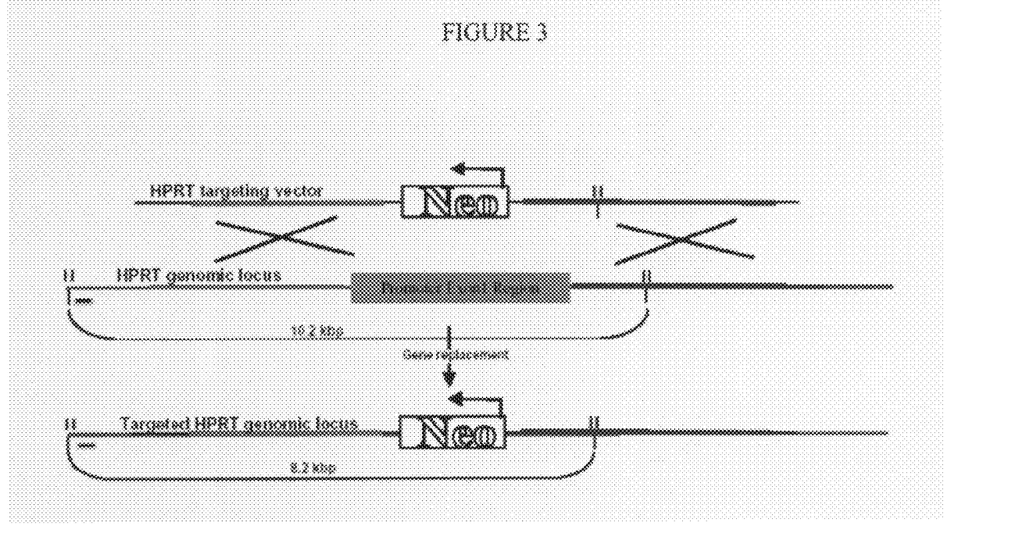
Figure 4:
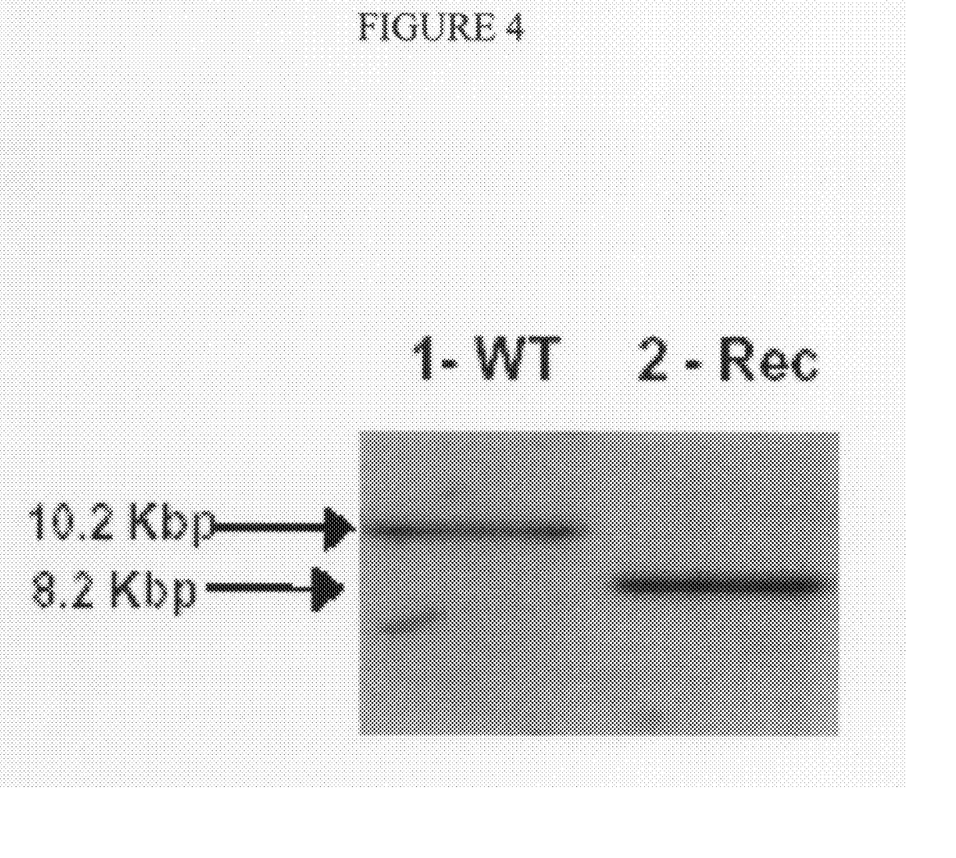

Brief definitions of nomenclature of targeting vectors are provided in this disclosure. The ends of the linear targeting vector with hairpin oligonucleotides are called hp-Target-hp. If NLSp is attached to one end, then it is named NLSp-hp-Target-hp. If one end contains NLSp and the other end contains the bait peptide, then it is called NLSp-hpTarget-hp-bait. Vectors available for deployment in the practice of this invention include hp-Target-hp, NLSp-hp-Targethp and the unmodified vector (Table 1). Briefly, the HPRT targeting plasmid was linearized with NotI and FseI enzymes thereby leading to DNA fragments with homologous cassettes and plasmid backbones. The digested product was resolved by agarose gel electrophoresis and the targeting cassette was purified by electroelution. Two hairpin oligonucleotides with 5' sticky ends, one for NotI and the other for FseI, were ligated to the ends of the targeting vector. Ligation of this hairpin to a linear vector created the hp-Target-hp vector. To the hairpin with a complementary 5' sticky end to the NotI site of the targeting vector, an NLSp peptide is attached and ligated to the NotI cohesive end of the plasmid. A hairpin was ligated to the FseI site creating the NLSp-hpTarget-hp vector. Hairpin formation, peptide coupling and ligation conditions are described in a subsequent example (infra). The three targeting vectors were transfected into an embryonic carcinoma F9 cell line (ATCC, Manassas, Va.) using Exgen 500, a polyethylenimine (PEI) transfecting reagent (Fermentas, Hanover, Md.). Two days after transfection, cells were subjected to G418 selection (400 ug/ml). Media was changed again on the third day. After 6 days, media was removed and media with double selection drugs G418 and 6-TG (2 uM) was added. Double-selection was followed for 7-10 days until colonies were visible. Colonies were picked and grown in a 24-well plate format. The gene targeting strategy is shown in FIG. 3 and genomic DNA was isolated to confirm the targeting event by Southern analysis and a representative blot is shown (FIG. 4).

Targeted HPRT Locus

To identify that the mutation in the HPRT gene was due to gene targeting, a Southern blot was performed which verified that a HR event occurred. A 5' probe was made by PCR amplification of the 200 bp DNA fragment from the region between HindIII and Acc651 (upstream of the 5' homologous arm region). This probe is depicted as a yellow box on the 5' end of HPRT genomic region (FIG. 3). FIG. 3 shows the screening strategy for the targeting event. A HindIII digestion of wild type genomic DNA produced a fragment of 10.2 Kb size by Southern blot using the 5' labeled probe (FIG. 4, lane 1). The targeted HPRT region has a deletion of the promoter-exon 1 region (4 Kb) and a replacement of a Neor selection marker cassette (~2 Kb size). Therefore, HindIII digestion of the targeted HPRT gene resulted in an 8.2 Kb DNA fragment (FIG. 4, lane 2). A Southern blot using a probe specific for the neomycin region resulted in the same size band (8.2 Kb) in genomic DNA from targeted cells (data not shown). This result is important since a random integration event would result in more than one band. FIG. 4 depicts a correctly targeted event. A correct targeting result is based upon use of the 5' and neomycin probes and Southern analysis. These results show that 6-TG selection is a powerful method for identification of HPRT targeting events.

TABLE 1

Enhancement of homologous recombination by attachment of an NLS peptide to the targeting vector.

| Exp. No. | Vectors | #F9 cells plated ($10^6$) | #G418/6-TG doubly resistant colonies | Overall recombination frequency ($\times 10^{-6}$) | Overall recombination frequency Mean ± SD ($\times 10^{-6}$) |
|---|---|---|---|---|---|
| 1. | Control | 4 | 1 | 2.5 | 2.2 ± 0.9 |
| 2. |  | 6 | 1 | 1.7 |  |
| 3. |  | 3 | 1 | 3.3 |  |
| 4. |  | 7 | 1 | 1.4 |  |
| 1. | hp-Target-hp | 9 | 1 | 1.1 | 2.1 ± 1.9 |
| 2. |  | 10 | 1 | 1.0 |  |
| 3. |  | 6 | 3 | 5.0 |  |
| 4. |  | 7 | 1 | 1.4 |  |

TABLE 1-continued

Enhancement of homologous recombination by attachment of an NLS peptide to the targeting vector.

| Exp. No. | Vectors | #F9 cells plated ($\times 10^6$) | #G418/6-TG doubly resistant colonies | Overall recombination frequency ($\times 10^{-6}$) | Overall recombination frequency Mean ± SD ($\times 10^{-6}$) |
|---|---|---|---|---|---|
| 1. | NLSp-hp-Target-hp | 0.9 | 3 | 33 | 13.7 ± 16.8 |
| 2. | | 4 | 1 | 2.5 | |
| 3 |  | 7 | 4 | 5.7 | |

F9 cell lines were transfected with targeting vectors with a structure as indicated; hp designates hairpin oligonucleotide; NLSp designates the peptide containing a nuclear localization signal. Transfected cells were subjected to G418 selection followed by 6-TG selection. Number of colonies formed after double selection is shown in column 4 by the # doubly resistant colonies. Overall recombination frequency equals the number of 6-TG/G418 doubly resistant colonies divided by the number of cells plated.

Table 1 shows the overall HR frequencies indicating efficient HPRT locus targeting and resultant HPRT inactivation. The HPRT targeting plasmid contains a neocassette; therefore, targeted cells are resistant to G418 and 6TG. The ratio of double resistant cells compared to total number of cells provides the overall HR frequency. The unmodified control and the hp-Target-hp (control for ends with hairpin only) have similar targeting frequencies. The NLSphpTarget-hp has approximately ten-fold more HR than do the control vectors demonstrating that the vector with NLSp efficiently localizes to the nucleus and provides more substrate for the recombination machinery. The attachment of bait peptides and NLSp to the vector and the assessment of their effects on HR frequency is described below.

EXAMPLE 2

Targeting Vectors Comprising a Peptide with a Nuclear Localization Signal and a Peptide Having a RAD51 Binding Domain Mouse ES cells are used for targeting experiments. The reason for using murine ES cells as a model in this example to improve homologous recombination ("HR") targeting is that any improvement in targeting efficiency in ES cells is expected to lead to increased ease in creation of myriad animal models of disease. One of the priority settings of the National Human Genome Research Institute is the "knockout mouse project" (NIH Planning Meeting for Knockout Mouse Project, May 24-25, 2006).

Figure 5:
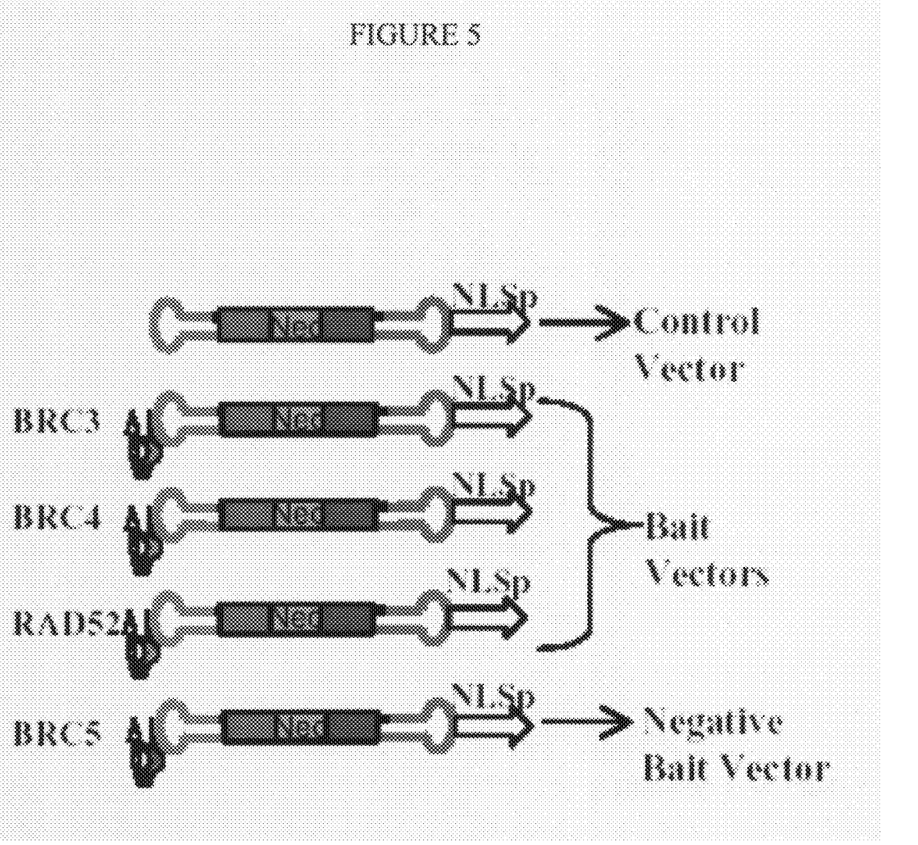

In this example, HR frequencies of a control targeting vector are compared to each of three different "bait" vectors that contain peptides, which bind to RAD51 (see FIG. 5). The control vector contained hairpin oligonucleotides at each end of the linear DNA molecule so as to block exonucleolytic attack. To enhance trafficking of the vector into the nucleus, a peptide with a nuclear localization signal is covalently attached to one of the hairpins. The bait vectors are identical except they also contain a RAD51 binding peptide covalently attached to the other hairpin oligonucleotide. A negative bait vector, which contains a defective bait peptide known not to interact with RAD51, is constructed as a control. These various vectors are electroporated into ES cells; both targeted and overall recombination frequencies into the HRPT locus is measured. Since the vectors carry a neomycin resistance gene, targeted recombination frequencies are the number of 6-TG resistant colonies (which also will be neomycin resistant) divided by the number of 6-TG and G418 doubly resistant colonies. Overall recombination frequencies are the number of 6-TG resistant colonies divided by the number of cells plated and subjected to drug selection. Selected 6-TG resistant colonies may be verified as resulting from HR by Southern blot analysis.

As discussed above, three proteins, RAD52, BRCA2 and RPA, are known to interact physically with RAD51 [21, 22, 27]. The amino acid sequences of the interacting domains from mouse RAD52 and mouse BRCA2 are used to synthesize the bait peptides (described below). Using chemically synthesized peptides, two domains within BRCA2 (the BRC3 and BRC4 repeats) were shown to bind RAD51, apparently at different regions of RAD51 (supra). Peptides corresponding to each will be utilized, as well as a peptide corresponding to the interacting domain from RAD52. Both the RAD52 binding domain and the BRC3 domain bind RAD51 at its N-terminal region, whereas the BRC4 domain appears to bind RAD51 at its nucleotide binding core [21, 27]. Since the BRC5 repeat domain apparently does not bind RAD51, a peptide corresponding to its sequence will be used for construction of the negative bait vector [49]. All peptides will be constructed with an additional cysteine residue at their C-termini so as to allow coupling to an alkylamino modified nucleotide within the loop region of the hairpin oligonucleotide.

EXAMPLE 3

Experimental Methods

Targeting Vector

A detailed description of HPRT vector construction is presented in Example 1. Briefly, a plasmid substrate containing a 5' homologous arm flanking the HPRT promoter region and a 3' homologous arm flanking exon 1 of the HPRT gene has been constructed (FIG. 2). The homologous arms bracket a neomycin resistance gene driven by the PGK1 promoter, which allows the constitutive expression of the Neor gene. The vector backbone contains unique restriction enzyme sites so that the ends of the targeting molecule can be ligated with hairpin oligonucleotides containing sequences complementary to the overhanging ends at the restriction sites. As described below, the various peptides are first covalently attached to the hairpin oligonucleotides before ligation of the hairpins onto the ends of the targeting vectors.

TABLE 2

Bait peptides for targeting experiments

| ¹Name (residues) | ²Amino acid sequence | Length |
|---|---|---|
| BRC3 (1391-1458) | SEQ ID NO. 1<br>ERNIKEFNIS FQTASGKNTR VSKESLNKSV NIFNRETDEL TVISDSLNSK ILHGINKDKM HTSSHKKAC | 69 |
| BRC4 (1485-1549) | SEQ ID NO. 2<br>YEIESTKEPT LLSFHTASGK KVKIMQESLD KVKNLSGETQ YVRKTASFSQ GSKPLKDSKK ELTLAC | 66 |
| RAD5 (294-344) | SEQ ID NO. 3<br>VAAKHAAVLP APPKHSTPVT AASELLQEKV VFPDNLEENL EMWDLTPDLE DC | 52 |
| ³BRC5 (1618-1688) | SEQ ID NO. 4<br>SSYPVTEDSA LAYYTEDSRK TCVRESSLSK GRKWLREQGD KLGTRNTIKI EC | 52 |

¹Residues in parentheses designate the position within the parent protein from which the peptide sequence is derived. The BRC peptides derive from mouse BRCA2 (Accession No. P97929): the RAD52 peptide derives from mouse RAD52 protein (Accession No. P43352).
²peptides will have a non-encoded cysteine (C) residue added to their C termini to facilitate coupling to an alkylamino group in the hairpin oligonucleotide. The serine residue in bold (S) indicated in the BRC3 and BRC4 peptides is changed from an encoded cysteine residue in the parent protein so as to ensure Cterminal coupling of the peptides to the hairpin oligonucleotide.
³BRC5 peptide does not interact with RAD51 and will be used as a negative bait control.

Peptides to be designed and used in this proposal will be derived from mouse protein sequences for use in murine ES cells. Using the Basic Local Alignment Search Tool 2 (BLAST2) [50], human and mouse BRC3, BRC4, BRC5 and RAD52 sequences have been aligned and corresponding sequences from mice have been chosen for peptide synthesis (listed in Table 2). The homologous human BRC3, BRC4, and BRC5 peptides (on average 70% identical in amino acid sequence to their respective mouse counterparts) showed no problems with solubility [27]. Mouse BRC3 and BRC4 each have an internal cysteine that will lead to crosslinking of the internal as well as C terminal cysteines. Therefore, the internal cysteine is changed to serine, which is structurally well tolerated when the cysteines are not involved in disulfide bridges. Alignment of the mouse BRC3 and BRC4 sequence to other species indicates that the internal cysteine is not conserved. The internal cysteine in mice is represented as serine in humans and monkeys, asparagine in dogs and histidine in hamsters. Similarly, BRC4 region alignment identified an internal cysteine represented as serine in monkeys and phenylalanine in humans and hamsters. Therefore, the internal cysteine is changed to serine. In order to help in the interpretation of experimental outcomes with respect to potential RAD51 binding of bait peptides, a vector is constructed to contain as bait the BRC5 peptide (murine amino acids 1618-1668), which has been shown to not interact with RAD51 [49]: therefore, a targeting vector with this negative bait peptide is expected to not have an elevated HR frequency. For a nuclear localization signal, a peptide from the SV40 large T antigen (NLSp) is used. The NLSp is synthesized (SEQ ID NO. 5: PKKKRKVEDPC) with an additional cysteine residue at its C terminus so as to allow coupling to an alkyamino modified nucleotide within the loop region of the hairpin oligonucleotide.

Amino-modified hairpin oligonucleotides (NotI-hp oligo [SEQ ID NO. 6]: 5' GGC CGC GAT GTG ACT CGC TTT* TTG CGA GTC ACA TCG C 3'; FseI-hp oligo [SEQ ID NO. 7]: 5' CCG ATG TGA CTC GTT T*TT CGA GTC ACA TCG GCC GG 3'; the indicated T* residue contains the free alkyl amino group) are. Oligonucleotide 5' ends are phosphorylated by a kinasing reaction for ligation.

The amino modified oligonucleotide is coupled to a peptide containing a C-terminal cysteine by use of the heterobifunctional crosslinking reagent sulfo SMCC, as described above. The crosslinker reagent contains an amine-reactive N-hydroxysuccinimide (NHS ester) and a sulfhydryl-reactive maleimide group. NHS esters react with primary amines at pH 7-9 to form stable amide bonds. Hairpin oligonucleotides with a free alkylamino group are reacted with the crosslinker to give a thiol-reactive maleimide oligonucleotide which in turn reacts with the C-terminal cysteine residue of the peptide leading to chemical coupling of the peptide-oligonucleotide [35].

Conjugation of peptides to hairpin oligonucleotides are monitored by polyacrylamide gel electrophoresis. Free and conjugated oligonucleotides are radiolabelled using $\alpha$-$P^{32}$-ATP nucleotide and T4 polynucleotide kinase. The various labeled molecules before and after proteinase K treatment are electrophoresed and visualization and quantification is performed with a Phosphorimager (Molecular Dynamics/GE Healthcare Bio-Sciences Corp. Piscataway, N.J.) in order to determine efficiency of conjugation. Unlabelled hairpin-peptide conjugates are simultaneously run in adjoining well for purification by electroelution from excised gel pieces. These purified conjugates are used for ligation to the targeting DNA.

The HPRT targeting DNA is generated by NotI plus FseI digestion of plasmid DNA followed by electroelution from agarose gels. End modification is accomplished by ligation to hairpin oligonucleotide(s) with or without attached peptides. The quality of the capped linear targeting DNAs is monitored by digestion with Exonuclease III (New England Biolabs, Beverly, Mass.) followed by electrophoresis on agarose gels and visualization with ethidium bromide. Vectors with hairpin oligonucleotides ligated to both ends are resistant to EXO III digestion whereas vectors with unmodified or one-end only modified vectors are susceptible to complete digestion. Thus, Exonuclease III digestion serves as a means to selectively and correctly purify capped targeting DNA molecules. One may normally start with 80 μg of plasmid DNA for hairpin modification. After exonuclease III digestion, greater than 80% linear plasmid is present capped at both ends and resistant to nucleolytic degradation. One can easily scale up the synthesis of modified plasmid DNA with no technical problems.

Maintenance of Undifferentiated ES Cells

ES cells are pluripotent and derived from the inner cell mass of the early embryo. When murine ES cells are cultured in the presence of leukocyte inhibitory factor (LIF), they remain undifferentiated and maintain the capacity to differentiate into any cell type. ES cells derived from 129/SvJ mice have been maintained in culture on a layer of feeder cells consisting of mitomycin C-treated primary mouse embryonic fibroblasts (MEF). The ES cells are cultured in ES medium (DMEM media supplemented with 15% serum [Hyclone, Logan, Utah], 1000 units/ml LIF [ESGRO from Chemicon, Temecula, Calif.], 1 mM sodium pyruvate, 1 mM nonessential amino acids, 0.1 mM 2-mercaptoethanol, 25 U/ml penicillin and 25 μg/ml streptomycin). For transfection studies, inactivated fibroblasts are removed. Briefly, to accomplish feeder cell removal, ES cells are passaged three times onto 0.1% gelatin-coated tissue culture plates and monitored for the presence of feeder cells. After three passages, the ES cell culture is devoid of feeder cells. An important point is that the ES cells used in this example do not require feeder cells and thereby act as feeder-independent ES cells. Inventor routinely cultures ES cells and uses 129/SvJ derived ES cells, which have been routinely used in the generation of knockout mouse models. However, other available ES cells (or multipotent progenitor cells) such as ES D3 (ATCC, Manassas, Va.) may be used in the practice of this invention.

Transfection and Scoring of Drug-Resistant Colonies

The linearized modified vectors are transfected into murine ES cells by electroporation. Briefly, ES cells ($1 \times 10^7$ in 800 µl of buffer) are electroporated (180 V, 500 uF) with 10 µg linearized HPRT targeting vector (FIG. 5). After electroporation, the cells are mixed with ES culture medium to a 5 ml volume and incubated (room temperature, 10 min). After incubation, the electroporated cells are plated onto 7 tissue culture dishes (10 cm), each coated with 0.1% gelatin at $1 \times 10^6$ cells per dish. After 24 h, one plate is trypsinized to determine the cell number that will be subjected to selection. The remaining 6 dishes receive G418 (400 µg/ml) and are allowed to grow for 5-6 days. Media is changed after 24 h and daily for the next 4 days during which time the majority of cell deaths occur in the selection phase. Three plates receive 2 µM of 6-TG in addition to G418 and allowed to grow for 10-12 days, the other three plates receive G418 for the remaining 12 days. Only cells with a targeted HPRT gene can grow in the presence of 6-TG. HPRT enzyme in the media is taken up by neighboring cells and incorporation of the 6-TG mediated by this exogenous enzyme leads to death of the bystander target cells. For this reason, culture dishes are replenished with fresh media containing 6-TG on a daily basis in the beginning until the majority of cell deaths is complete. The G418 plate is stained with crystal violet, the number of colonies is determined and this number is used in calculations of G418 resistant colonies. After 12 days, surviving colonies that are doubly resistant to G418 and 6-TG are picked and grown in a 24 well plate. The DNA is isolated and analyzed by Southern blot to confirm targeting events at the HPRT locus as described above.

The HPRT targeting vector contains a neomycin resistance marker flanked on either side by HPRT homologous DNA regions that direct recombination into the endogenous HPRT locus. Therefore, after transfection, both random and targeted integration events by the vector can confer resistance to the antibiotic G418. When the cells are grown in the presence of G418 plus 6-TG, only HR targeted cells will grow. As discussed previously, the targeting recombination frequency is defined as the number of doubly resistant 6-TG/G418 colonies divided by the sum of the number of G418-only resistant colonies plus 6TG/G418 doubly resistant colonies. The overall recombination frequency is defined as the number of doubly resistant 6-TG/G418 colonies divided by the number of cells plated and subjected to drug selection.

There are at least two different outcomes that signify that the addition of a bait peptide to the targeting DNA is beneficial for HR (summarized in Table 3). First, the bait may increase the efficiency of HR without eliciting much effect on random integration of the vector. We would see an increase in the number of 6-TG/G418 double resistant colonies without much change in the number of G418-only resistant colonies. In comparison to the control vector, both the overall and targeted recombination frequencies increase (scenario 1, Table 3). It is possible, however, that by diverting more of the transfected DNA into the HR pathway, the addition of bait suppresses random integration. In that case, the number of G418-only resistant colonies decreases. Whether that diversion concomitantly increases HR, although likely, is not certain—i.e., the number of 6-TG/G418 doubly resistant colonies may or may not increase. Thus, for this outcome (scenarios 2A and 2B, Table 3) the targeted recombination frequency increases, in comparison to the control vector, but the overall recombination frequency either increases as well or remains relatively unchanged.

There are three different outcomes from which we may conclude that a particular bait is ineffective for specifically promoting HR. First, the bait is inert, in which case we would observe no significant changes in either the targeted or overall recombination frequencies compared to the control vector (scenario 3, Table 3). Next, the addition of bait to a targeting DNA may non-specifically "poison" all integration events— i.e., both the numbers of 6-TG/G418 doubly resistant colonies and G418 singly resistant colonies decrease. In that case (scenario 4, Table 3), the overall recombination frequency would decrease, but the effect on targeted recombination frequencies might be variable depending on the relative efficiency of poisoning the HR versus the random integration pathways. The third potential negative outcome is that the addition of bait to a targeting DNA improves non-specifically both HR and random integration of the baited vector—i.e., both the numbers of 6-TG/G418 double resistant colonies and G418 single resistant colonies increase compared to the control vector. Here, we would see an increase in the overall recombination frequency but little significant change in the targeted recombination frequency (scenario 5, Table 3).

TABLE 3

Model Experiment to Illustrate Potential Experimental Outcomes for a Particular Baited Vector

| Scenario | Interpretation | # ES cells plated | # G418-singly resistant colonies | # G418/6-TG doubly resistant colonies | Overall recombination frequency ($\times 10^{-6}$) | Targeted recombination (%) |
|---|---|---|---|---|---|---|
| 1 | HR promoted | $1 \times 10^6$ | 400 | 100 | 100 | 20 |
| 2A | Random Integration suppressed, HR high | $1 \times 10^6$ | 40 | 100 | 100 | 71 |
| 2B | Random integration suppressed, HR unchanged | $1 \times 10^6$ | 40 | 10 | 10 | 20 |

TABLE 3-continued

Model Experiment to Illustrate Potential Experimental Outcomes for a Particular Baited Vector

| Scenario | Interpretation | # ES cells plated | # G418- singly resistant colonies | # G418/6-TG doubly resistant colonies | Overall rocombination frequency ($\times 10^{-6}$) | Targeted recombination (%) |
| --- | --- | --- | --- | --- | --- | --- |
| 3 | Inert | $1 \times 10^6$ | 400 | 10 | 10 | 2.4 |
| 4 | Both random and HR poisoned | $1 \times 10^6$ | ≦40 | 1 | 1 | ≧2.4 |
| 5 | Both random and HR promoted | $1 \times 10^6$ | 4000 | 100 | 100 | 2.4 |
| Control | | $1 \times 10^6$ | 400 | 10 | 10 | 2.4 |

Overall recombination frequency equals number of 6-TG/G418 doubly resistant colonies divided by total number of cells subjected to selection. Targeted recombination frequency equals number of 6-TG/G418 doubly resistant colonies divided by the sum of G418-singly resistant plus 6-TG/G418 doubly resistant colonies. Control vector contains the NLS-peptide-hairpin oligonucleotide at one end and a hairpin oligonucleotide at the other end of the linear targeting vector. Baited vector is identical except that it contains the bait attached to the hairpin oligonucleotide at the other end.

EXAMPLE 4

Targeting Vectors Designed to Cooperatively Bind RAD51 at Two Different Sites on that Protein. In Addition, These Vectors Contain a Nuclear Localization Signal A vector with two different bait peptides that each interact with different regions on RAD51 has potential for increased RAD51 recruitment and therefore increased HR frequency. Low affinity interactions between the peptides and RAD51 may nevertheless lead to tight binding due to cooperativity. The BRC3 and RAD52 peptides interact with the N-terminal domain of RAD51 whereas the BRC4 peptide interacts with the nucleotide binding region of RAD51. Double bait targeting vectors containing the BRC4 peptide in combination with either the BRC3 or RAD52 peptide may thus be more effective for recruitment of RAD51 onto the targeting DNA. One of the bait peptides will also have an NLS sequence at its N terminus thereby causing it to have a dual function, namely as bait and also for targeting the vector to the nucleus. Hybrid proteins with NLS have been shown to enter the nucleus and retain function [51]. As in the preceding examples, HR frequencies (both targeted and overall) of these dual bait vectors are compared to the control vector containing only the NLS peptide in transfection of ES cells.

A NLS-BRC4 hybrid peptide is synthesized with intervening amino acids of glycine, serine and glycine (underlined region in the following sequence) between the NLS and BRC4 sequences. Its amino acid sequence is (SEQ ID NO. 8): PKKKRKVEDP GSG YEIESTKEPT LLSFHTASGK KVKIMQESLD KVKNLSGETQ YVRKTASFSQ GSKPLKDSKK ELTLAC. It is attached to the targeting vector at one end whereas either the RAD52 or BRC3 peptide is attached to the other end as described in the preceding examples, thus generating the two double bait vectors to be tested. As discussed previously, the internal cysteine residues contained within the BRC3 and BRC4 peptides is changed to serines so as to ensure C-terminal coupling of the peptides to the hairpin oligonucleotides.

If the dual vectors are effective in driving transfected DNA into the HR pathway, the skilled artisan would reasonably expect to observe either an increase in overall HR frequencies and/or increased targeted HR frequencies, as discussed in the preceding example, in comparison to the control vector.

EXAMPLE 5

Bioprocess, Veterinary and Medical Application

Autologous hematopoietic cells have been used as targets of gene transfer with applications to cell therapy as well as treatment of inherited disorders and acquired immunodeficiencies. This homologous recombinant system is applicable to the genetic therapy of any and all genetic disorders, or to the production of organisms having particular desired traits for industrial and commercial application.

For example, an initial application of this invention is the chronic granulomatous disease (CGD) model that is a group of inherited disorders characterized by recurrent and often life-threatening suppurative infections as well as chronic inflammation with granuloma formation. The disease, which has an estimated incidence of 1 in 250,000 individuals, results from mutations in any one of 4 subunits of a nicotinamide adenine dinucleotide phosphate (NADPH) oxidase found in neutrophils and other phagocytic leukocytes. Murine CGD appears to be a good model for the human disease, with defects in both host defense and inflammation that are similar to their human counterpart. One-third of the cases of CGD result from defects in the gene encoding p47$^{phox}$. For example, CGD mice exhibit an increased susceptibility to infection with *S aureus, B cepacia,* and *A fumigatus.* Malech et al showed that the CGD mouse model (p47$^{phoxi-/-}$) can be corrected by human p47$^{phox}$. Bone marrow progenitor p47$^{phoxi-/-}$ cells transfected with a retroviral vector encoding the human form of p47$^{phox}$, upon transplantation into p47$^{phoxi-/-}$ mice, restore the oxidant-dependent host defense function of phagocytes. In the current project, the above-described CGD mouse model will be utilized for targeting of the human p47$^{phox}$ gene to the docking site HPRT locus of the progenitor cells using the highly efficient targeting method defined in this grant application. Targeted progenitor cells will be isolated by the 6-thioguanine-selection method and the enriched cell population will be transplanted into animals and assessed for oxidant-dependent host defense function of phagocytes.

What is claimed is:

1. A targeting vector for homologous recombination, comprising:
   (a) a polynucleotide that encodes a gene-product-of-interest;
   b) a proximal polynucleotide having a sequence that is homologous to a proximal part of a target polynucleotide;
   (c) a distal polynucleotide having a sequence that is homologous to a distal part of a target polynucleotide;
   (d) a nuclear localization signal ("NLS") attached to the end of either the proximal polynucleotide or the distal polynucleotide;
   (e) a first bait polypeptide attached to the end of either the proximal polynucleotide, wherein the NLS sequence is attached to the distal polynucleotide, or the distal polynucleotide, wherein the NLS sequence is attached to the proximal polynucleotide, wherein the first bait polypeptide binds to RAD51; and
   (f) a second bait peptide positioned between the proximal or distal polynucleotide, and the NLS, wherein the second bait polypeptide and the NLS comprise a combined sequence as set forth in SEQ ID NO: 8.

2. The targeting vector of claim 1 wherein the gene-product of interest is a cellular marker.

3. The targeting vector of claim 2 wherein the cellular marker is selected from the group consisting of beta lactamase, neomycin resistance, green fluorescent protein, and luciferase.

4. The targeting vector of claim 1 wherein the gene-product of interest is a protein.

5. The targeting vector of claim 4 wherein the protein is selected from the group consisting of IL-2 receptor γ chain, deaminase, and nicotinamide adenine dinucleotide phosphate oxidase.

6. The targeting vector of claim 1 wherein the target polynucleotide is hypoxanthine-guanine phosphoribosyltransferase ("HPRT").

7. The targeting vector of claim 1 wherein the target polynucleotide is selected from the group consisting of a polynucleotide that encodes any one of IL-2 receptor γ chain, deaminase, and nicotinamide adenine dinucleotide phosphate oxidase.

8. The targeting vector of claim 1 wherein the bait polypeptide comprises a sequence set forth in any one of SEQ ID NO: 1, SEQ ID NO: 2 and SEQ ID NO: 3.

9. The targeting vector of claim 1, wherein the targeting vector comprises a cap on the end of each one of the proximal polynucleotide and the distal polynucleotide.

* * * * *